United States Patent [19]
Alt

[11] Patent Number: 6,029,422
[45] Date of Patent: Feb. 29, 2000

[54] ANTISEPTIC DISPOSABLES AND METHODS FOR MEDICAL AND SURGICAL PROCEDURES

[75] Inventor: Eckhard Alt, Ottobrunn, Germany

[73] Assignee: Sulzermedica USA, Inc., Houston, Tex.

[21] Appl. No.: 09/245,915

[22] Filed: Feb. 8, 1999

Related U.S. Application Data

[62] Division of application No. 08/648,216, May 15, 1996, Pat. No. 5,868,245.

[51] Int. Cl.⁷ .................................................. B65B 55/22
[52] U.S. Cl. ............................. 53/431; 53/425; 53/445; 53/449; 53/474
[58] Field of Search .............................. 53/155, 238, 239, 53/425, 426, 431, 445, 449, 474

[56] References Cited

U.S. PATENT DOCUMENTS

| | | |
|---|---|---|
| 2,335,015 | 11/1943 | Lantheaume . |
| 2,699,779 | 1/1955 | Lustig . |
| 3,635,567 | 1/1972 | Richardson . |
| 3,685,645 | 8/1972 | Kawaguchi . |
| 3,923,154 | 12/1975 | Tulis et al. . |
| 3,939,971 | 2/1976 | Tulis . |
| 3,942,634 | 3/1976 | Gandi et al. . |
| 4,128,173 | 12/1978 | Lazarus et al. . |
| 4,226,328 | 10/1980 | Beddow . |
| 4,379,506 | 4/1983 | Davidson . |
| 4,437,567 | 3/1984 | Jeng . |
| 4,497,402 | 2/1985 | Karos . |
| 4,665,901 | 5/1987 | Spector . |
| 4,777,780 | 10/1988 | Holzwarth . |
| 4,811,847 | 3/1989 | Reif et al. . |
| 4,813,210 | 3/1989 | Masuda et al. . |
| 4,878,903 | 11/1989 | Mueller . |
| 4,928,830 | 5/1990 | Brewer . |
| 5,054,610 | 10/1991 | Ajello . |

FOREIGN PATENT DOCUMENTS

| | | |
|---|---|---|
| 0485345 | 5/1992 | European Pat. Off. . |
| 1455670 | 11/1976 | United Kingdom . |
| 2059268 | 4/1981 | United Kingdom . |
| 90/04985 | 5/1990 | WIPO . |
| 94/13354 | 6/1994 | WIPO . |

*Primary Examiner*—Daniel B. Moon
*Attorney, Agent, or Firm*—Blank Rome Comisky & McCauley LLP

[57] ABSTRACT

A method of preventing or reducing the incidence of staphylococci and other infections as a result of surgical or medical treatment procedures is implemented by inserting into or attaching to each sterile package containing a tool, implement, or implantable for use in such a procedure at least one impregnable swab containing a solution of $H_2O_2$ packaged in a separate sterile pack, for use by the surgeon, therapist, or assistant in wiping down the tool, implement, or implantable, as the case may be, before use to maintain the sterility thereof in such procedure. The solution of $H_2O_2$ is in a concentration of about 3% by volume. A plurality of separate sterile packs may be inserted in or attached to the sterile package, in which each of the sterile packs contains at least one swab impregnated with a solution of $H_2O_2$ in such concentration. Additionally, at least one separate sterile pack may be inserted in or attached to the sterile package containing at least one swab impregnated with a saline (NaCl) solution for use in wiping down the tool, implement, or implant after wiping same with a swab containing the $H_2O_2$ solution. If the implantable is to be used within about one month or so from the time of its assembly into the sterile package, it may be wiped down with the $H_2O_2$ solution before it is assembled in the sterile package, and in that event, no separate sterile packs of $H_2O_2$ solution or NaCl solution need be included in or with the sterile package.

15 Claims, 1 Drawing Sheet

ANTISEPTIC DISPOSABLES AND METHODS FOR MEDICAL AND SURGICAL PROCEDURES

CROSS-REFERENCE TO RELATED APPLICATION

This application is a division of application Ser. No. 08/648,216, filed May 15, 1996, now U.S. Pat. No. 5,868, 245.

BACKGROUND OF THE INVENTION

The present invention relates generally to medical and surgical devices and procedures, in which devices are temporarily or permanently implanted within the patient's body or are used for performing surgery on the patient's body, or are used for transporting blood and other fluids from or to the patient's body by means of catheters or other transporting devices. More particularly, the invention relates to disposable antiseptic wipes or impregnated pads which are packed within packages used for shipping and storing such medical and surgical devices.

Patients who undergo surgery of various kinds including implantation of devices such as catheters, leads, pacemakers, defibrillators, stents, and a wide variety of other devices or materials all to often suffer massive infection as a consequence of the use of aseptic materials. This occurs despite supplier packaging of the implantables or surgical tools in sterile packaging and the use of sterilizing radiation and the like, as well as the strict observation of aseptic requirements by the surgeons, nurses, and others involved in operating room procedures.

In this respect, it should be noted that surgical techniques have greatly improved during the last decade. Continuously collected knowledge and experience and standardization of operating methods has led to a dramatic reduction in risk of failure associated with even complex operations. In case of implantation of pacemakers, for example, increased knowledge and experience has led to a dramatic reduction in mortality, which at the present time ranges to 0.1% or even lower. Other problems such as functional problems have been reduced with an increased technical capability of the devices and enhanced electrode techniques. Therefore, the major problem that remains with implantation of medical interventional devices, such as cardiac pacemakers and defibrillators, is the risk of infections.

Several factors are associated with the infection of implantable devices, such as operation time, trauma to the tissue, the presence of a hematoma, presence of diabetes, increased age, and implantation of dual chamber devices. The reason for the increased number of infections with implantable cardiac pacemakers of dual chamber type is not simply the longer time required to perform the operation, which on average is only ten to fifteen minutes longer than that for a single chamber unit, but the increased number of foreign body biomaterials (biocompatible materials) that are part of the implanted device(s).

Recent studies have shown that these biomaterials, such as silicone or polyurethane, which are implanted in the human body, play a major part in the increased risk for infection. Recently gathered knowledge of the role of the polymer structure has led to a finding that microbiological germs such as *staphylococcus epidermitis*, or *staphylococcus albus* (as the same germ is also called), tend to settle preferentially on plastic material such as silicone or polyurethane insulation. The manner in which these germs nest on the surface is by quickly building a barrier of mucus, by which they become protected from any further action of systemically produced or introduced antibiotics. It has been found that the perioperative prophylaxis with a one-time antibiotic is helpful in reducing the number of infections. Nevertheless, there remain a number between 3% and 7% of devices for which infection occurs despite the use of great care by the implanting physician.

It is a principal aim of the present invention to provide means and methods by which to reduce the incidence and severity of infection in the course of or as a result of surgical or medical procedures, and to do so in a very simple, safe, and effective manner.

SUMMARY OF THE INVENTION

Briefly, the invention resides in the use and provision for use of sterile swabs or wipes impregnated or saturated with hydrogen peroxide ($H_2O_2$), the swabs being packed in their own sterile packs for insertion within the same sterile packages in which the surgical or medical devices are supplied for use in surgical or medical procedures on and/or for implantation in the patient, for wiping down the respective devices prior to implantation thereof.

By packing such $H_2O_2$ swabs or wipes in individual packs with the surgical devices or materials, for immediate and convenient availability to the surgeon and assisting personnel in the operating room or treatment room who may be required to handle those tools, implements, or implantables to be used in the procedure, a much greater likelihood exists that these tools, implements and implantables will be given a sterile wipedown immediately prior to their use in the surgical or medical procedure.

The swab or wipe is preferably packaged in a solution of 3% by volume of $H_2O_2$ in a wet gauze, the packaging of the swab(s) being performed under sterile conditions using aluminum foil or the like to prevent the gauze from drying out. Each swab pack is intended to be opened at the time of implant or other use of a device or material, for the purpose of cleaning the apparatus, device, or material, such a lead, a pacemaker, a defibrillator, or other implantable device—and is preferably also packed together (but in a separate sterile pack) with 0.9% saline solution to rinse off the $H_2O_2$ later on.

The applicant has conducted studies which demonstrate clearly that such simple wipe-down of the implantable device, or of apparatus or material to be used in transporting fluids into or from the patient's body, as a pre-operating or pre-treatment procedure, can significantly reduce the incidence of serious staphylococcus and other infections that all too often result from surgical or related patient procedures in hospitals and medical centers. From these studies, a reduction of 90% or more in infection rate has been observed, from the typical rate found in hospitals and medical centers, which do not presently use or require pre-surgical or pre-treatment wipe-down with $H_2O_2$.

Therefore, a more detailed aim or object of the present invention is to provide a method and means for reducing or eliminating infection through a pre-surgical or pre-treatment wipe-down with $H_2O_2$ of devices to be implanted in, or used in procedures involving introduction or removal of materials to or from, the body of a patient.

BRIEF DESCRIPTION OF THE DRAWINGS

The above and other aims, objects, features, aspects, and attendant advantages of the invention will become apparent from a consideration of the following detailed description of a presently contemplated best mode of practicing the invention, by reference to a preferred embodiment and method, taken in conjunction with the accompanying drawings in which.

DETAILED DESCRIPTION OF THE PREFERRED EMBODIMENT AND METHODS

Figure 1A:
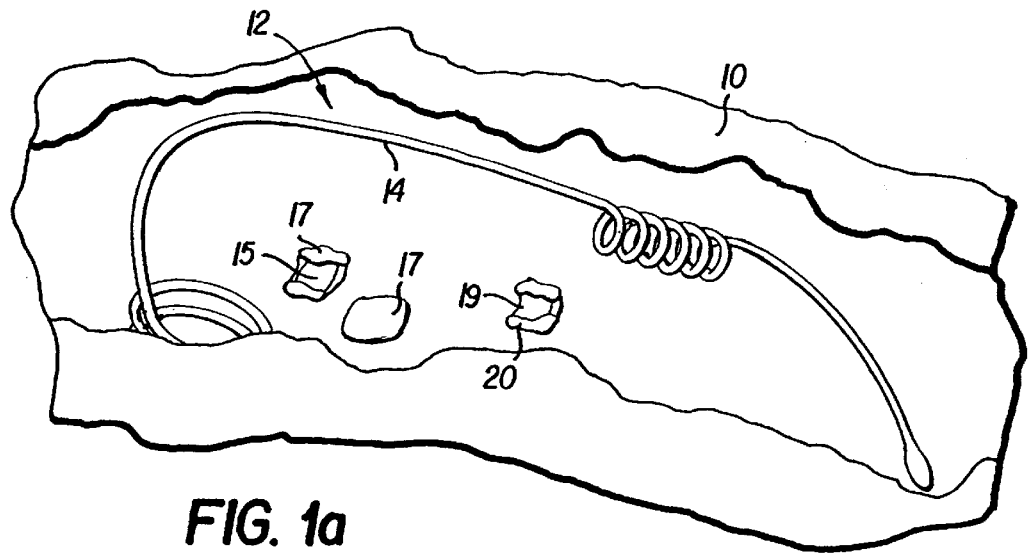
FIG. 1a is a simple partial perspective broken-away view of a sterile package for a lead with electrodes for implantation with a pacemaker or defibrillator, for example, in which one or more sterile packs of $H_2O_2$ swabs and separate NaCl swabs are inserted.

Referring now to FIG. 1a, a sterile package 10 contains a tool, implement, or implantable 12 which is to be used in a surgical procedure performed in an operating room. In this particular example, the implement is a lead 14 which may, for example, be intended for use with a cardiac pacemaker pulse generator/defibrillator to be implanted in a cardiac patient.

In a preferred embodiment of the invention, a swab 15, such as a gauze swab, which is impregnated or saturated with a solution of $H_2O_2$ in a concentration of 3% by volume and packed in its own separate sterile pack 17 such as aluminum foil, is contained within the sterile package for the lead 14. Preferably, a separate swab 19 consisting of a gauze impregnated with 0.9% saline (NaCl) solution packed in its own sterile pack 20 of aluminum foil is also inserted in or attached to the sterile package 10 to rinse off the $H_2O_2$ after its use.

Figure 1B:
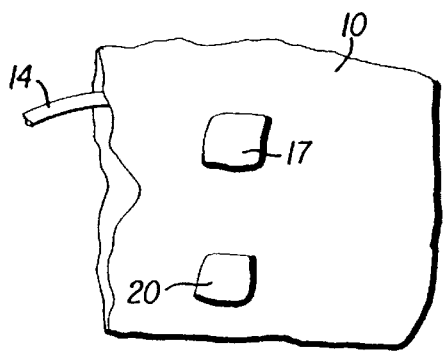
FIG. 1b is a fragmentary view similar to that of FIG. 1a, showing sterile packs of an $H_2O_2$ swab and NaCl swab attached to the exterior of a sterile package in which the lead is contained.

In an alternative embodiment, shown in FIG. 1b, the sterile pack 17 containing the swab 15 impregnated with the solution of $H_2O_2$ is secured to the outside of sterile package 10 by means of an adhesive. Another sterile pack 20 containing a swab 19 impregnated with the NaCl solution is also secured to the exterior of sterile package 10 by adhesive. In this embodiment, the sterile packs, both 17 and 20, should be adequately secured to the sterile package 10 to prevent them from being dislodged in ordinary handling.

Figure 2:
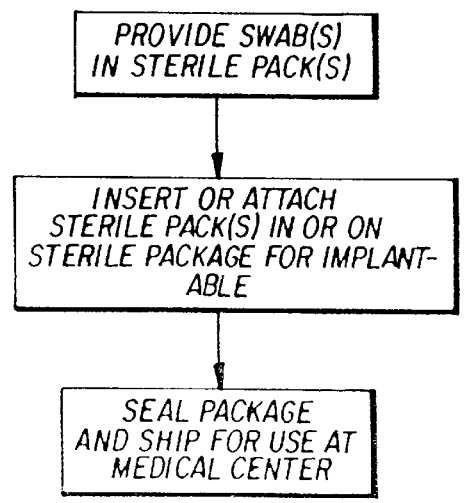
FIG. 2 is a flow diagram illustrating the method in which the sterile packs of $H_2O_2$ swabs are provided for use by the surgeon or persons assisting in the operating or treatment room.

This procedure is also shown in the flow chart of FIG. 2, which does not require further explanation.

In practice, the swab or wipe (e.g., cotton gauze pad of appropriate dimensions) containing the $H_2O_2$ solution (e.g., 3% or more in water) is supplied in a sterile pack with the lead or pacer (or other implantable device, or apparatus, tool, or implement being used in the surgical or medical treatment procedure of interest), to make it especially convenient for the surgeon or person assisting to apply the $H_2O_2$ to the lead or pacer just prior to an implantation procedure, or to the other apparatus or device just prior to their use in a procedure involving introduction or removal of materials to or from the body of a patient such as a blood transfusion. Preferably, two or three $H_2O_2$ swabs in a single pack or in separate packs may be inserted in the sterile package containing an implantable, together with at least one saline (e.g., 0.9% in water) impregnated pad in its own sterile pack as well.

Then, after the device's sterile package is opened prior to performing the procedure, the $H_2O_2$ wipes may be used first to wipe down the device, followed by and neutralized by a second wipe-down with the 0.9% NaCl swab. The saline swab is used because $H_2O_2$ has some toxicity to body tissue, so it is desirable to remove it or neutralize it to a large extent after it has been applied to the devices used in the implant procedure to render them antiseptic.

Although the use of the $H_2O_2$ swabs has been specifically described herein in connection with procedures for the implantation of cardiac pacemakers or defibrillators and leads therefor, the same usage of such swabs would apply to anything that is implantable, or used in connection with surgery, or in treatment of a patient involving a penetration of the skin such as for exchange of fluid in blood transfusion, dialysis, or chemotherapy, for example, or introduction of leads, catheters, or prostheses, whether for temporary or long term therapy or treatment. For example, implantable prostheses such as hip joints, and other metal or plastic implants are also prime candidates for use of $H_2O_2$ swabs. As indicated above, the use of such swabs in this manner—that is, before the procedure is commenced—has been found to have a very beneficial effect on preventing or significantly reducing the incidence of infection.

For example, despite stringent efforts to avoid infection during pacemaker/defibrillator implantation, perioperative infection attributable to *S. epidermis* has been observed in up to 5% of the cases, and typically in about three cases out of every 100. In tests conducted by the applicant, standard pacemaker and defibrillator lead materials (e.g., polyurethane and silicon rubber) were sterilized with gas. Each was then contaminated with bacteria, specifically *S. epidermis* in concentration of 1E5 or 1E7 bacteria per milliliter in NaCl solution 9%, for a total contamination time of 2 hours (h) at 37° C. After contamination, each lead was rinsed with 0.9% NaCl, and each was then wiped with $H_2O_2$ using a gauze pad containing the solution. Alternatively, the rinse with NaCl was performed by wipe-down of the lead with a separate gauze pad impregnated with a 0.9% solution thereof after the wipe-down with the $H_2O_2$ pad. A lead wiped only with NaCl and another which was untreated (not subjected to contamination) were employed in each of the tests as control elements. The wipe with $H_2O_2$ was varied as to the parameters of: treatment before or after contamination; concentration of $H_2O_2$ in solution of 1.5%, 2%, and 3%; and total contamination time of 2 h and 4 h.

The results of treatment of the leads with 3% $H_2O_2$ after contamination showed a near total reduction in bacteria colony, and virtually the same result was observed for leads treated before contamination, compared to the control leads (untreated or with only NaCl wipe). While the other concentrations had an effect, the greatest was seen with 3% $H_2O_2$. It was concluded that treatment of the implantables with the $H_2O_2$ solution drastically reduces the numbers of bacteria that would otherwise lead to infection in a significant percentage of implant patients as a result of the surgery. It is postulated, in part from clinical results on a sampling of patients who received implants treated in the above manner, that the rate of infection drops from about 3% typical to about 0.25%, from use of an $H_2O_2$ wipe of the implantables and other implements used in the surgery.

The applicant has found that even if the implant is wiped with the $H_2O_2$ swab(s) once or twice and then wiped with the saline solution before contamination, the $H_2O_2$ continues to be effective. It is not completely clear as to how or why this happens, but the process has been found to be effective in clinical tests. Apparently, the $H_2O_2$ changes the surface structure or characteristics of the polymer or other material used in the lead, for example, which disturbs the propensity for adhesion of germs to the implant after the wiping, even after it has been neutralized by the saline solution wipe.

If the implantation is to be performed within about one month or so after the sterile package of the implant is assembled, the implant may be wiped down with the $H_2O_2$ solution and rinsed with the NaCl solution before it is assembled into the sterile package, and in that case, separate sterile packs of $H_2O_2$ or NaCl pads need not be included with the sterile package. In that respect, the applicant's studies indicate, surprisingly, that the $H_2O_2$ remains active even if the device, e.g., a lead, was wiped with the $H_2O_2$ swab as much as about one month or so prior to the operation or treatment in which the device is used. That is, despite such relatively lengthy period between the wipe-down of the device with $H_2O_2$ and the use of the device, the infection rate is still reduced by up to about 90%. Two effects appear to be present, viz., one of which is an acute toxic effect when the device is wet with the $H_2O_2$ solution, and the second of which provokes a change in the surface characteristics of the device to prevent adhesion of bacteria to the surface of the device.

Although $H_2O_2$ is a staple of virtually every home medicine cabinet, for use in cleansing wounds, as an antiseptic, to the applicants' knowledge no one has heretofore considered that it might be useful as an infection fighter by use in wiping down a foreign (to the body) material or implement prior to its being used in surgery on or implanted in the patient's body.

Although a presently contemplated best mode of practicing the invention has been described in terms of a presently preferred embodiment and method thereof, it will be apparent to those skilled in the field or art to which the invention pertains that variations and modifications of this embodiment and method may be made without departing from the spirit and scope of the invention. It is therefore intended that the invention shall be limited only as required by the appended claims and the rules and principles of the applicable law.

What is claimed is:

1. A method for preventing or reducing the incidence of staphylococcus and other bacterial infection of a patient undergoing a surgical or medical treatment procedure, said method comprising the steps of impregnating a material swab with a wet solution of $H_2O_2$; packaging the $H_2O_2$ impregnated swab in a sterile pack; and packing said sterile pack together with a tool, implement, or implantable to be placed in contact with blood and tissue of the patient's body during at least a part of said surgical or medical treatment procedure; wherein said tool, implement or implantable is packaged to maintain the sterility thereof during shipping, storage and handling prior to use in said treatment procedure, and said solution of $H_2O_2$ contains an adequate concentration of $H_2O_2$ to disinfect said tool, implement or implantable upon wipe down thereof with the $H_2O_2$ impregnated swab after removal from said sterile pack and prior to use of said tool, implement or implantable in said treatment procedure.

2. The method of claim 1, wherein said solution of $H_2O_2$ has a concentration of at least about 1% $H_2O_2$ by volume.

3. The method of claim 2, wherein said solution of $H_2O_2$ has a concentration of about 3% $H_2O_2$ by volume.

4. The method of claim 1, wherein said step of packing includes inserting or attaching said sterile pack in or to a sterile package containing said tool, implement or implantable.

5. The method of claim 1, including impregnating another swab with a solution containing a neutralizing agent for a subsequent wipe down to neutralize the $H_2O_2$ and potential toxicity thereof remaining from the first wipe down before placing the tool, implement or implantable in contact with blood and tissue of the body; and packaging said neutralizing agent impregnated swab in an additional sterile pack for packing together with the first-mentioned sterile pack and the tool, implement or implantable.

6. The method of claim 5, wherein said neutralizing agent is a wet solution of saline (NaCl); and wherein the step of packing said additional sterile pack containing the NaCl swab together with the first-mentioned sterile pack and the tool, implement or implantable is performed by inserting or attaching said additional sterile pack in or to a sterile package containing the tool, implement, or implantable.

7. The method of claim 6, wherein said solution of NaCl has a concentration of at least about 0.9% NaCl by volume.

8. A method of providing a sterile package for a device to be placed in direct contact with blood and tissue of the body of a patient in a surgical or medical treatment procedure performed on the patient, comprising the steps of providing a container, enclosing said device within the container to maintain device sterility during shipping, storage and handling of the container prior to opening thereof, impregnating an absorbent pad with a solution having a predetermined concentration of a disinfectant expressly for swabbing the surface of said device which is to be placed in contact with blood and tissue of the patient with the impregnated pad to apply the disinfectant solution to said surface after removal of the device from said container just prior to commencing said treatment procedure, to prevent said surface of the device from being contaminated by harmful bacteria before the placement is made, enclosing said impregnated pad within a sterile pack, and assembling the sterile pack having said impregnated pad therein with said container for shipment therewith.

9. The method of claim 8, wherein the step of assembling the sterile pack with the container is performed by enclosing the sterile pack within the container.

10. The method of claim 8, wherein the step of assembling the sterile pack with the container is performed by securely attaching the sterile pack to the container.

11. The method of claim 8, wherein said disinfectant is $H_2O_2$.

12. The met hod of claim 11, wherein said predetermined concentration of $H_2O_2$ is about 3% by volume in water.

13. The method of claim 11, further including impregnating a second absorbent pad with a solution having a predetermined concentration of a neutralizer of $H_2O_2$ expressly for swabbing the surface of said device with the neutralizer solution in the second pad after application of the disinfectant solution thereto by first swabbing said surface of the device with the first-mentioned pad, for neutralizing the $H_2O_2$ on said surface before placement of the device in direct contact with blood and tissue of the body, and enclosing said second impregnated pad in a second sterile pack for assembly with said container for shipment therewith.

14. The method of claim 13, further including the step of assembling the sterile pack with the container by enclosing the sterile pack within the container.

15. The method of claim 13, further including the step of assembling the sterile pack with the container by securely attaching the sterile pack to the container.

* * * * *